US00PP16764P2

(12) United States Plant Patent
Danziger

(10) Patent No.: US PP16,764 P2
(45) Date of Patent: Jul. 4, 2006

(54) **DOUBLE *IMPATIENS* PLANT NAMED 'DANDOCHESAL'**

(50) Latin Name: *Impatiens walleriana*
Varietal Denomination: DANDOCHESAL

(75) Inventor: Gabriel Danziger, Moshav Nir-Zvi (IL)

(73) Assignee: Daziger "Dan " Flower Farm, Post Beit Dagan (IL)

( * ) Notice: Subject to any disclaimer, the term of this patent is extended or adjusted under 35 U.S.C. 154(b) by 0 days.

(21) Appl. No.: 11/036,338

(22) Filed: Jan. 18, 2005

(51) Int. Cl.
*A01H 5/00* (2006.01)

(52) U.S. Cl. ..... Plt./317
(58) Field of Classification Search ..... Plt./317
See application file for complete search history.

*Primary Examiner*—Anne Marie Grunberg
*Assistant Examiner*—Annette H Para
(74) *Attorney, Agent, or Firm*—Foley & Lardner LLP

(57) ABSTRACT

A new and distinct Double *Impatiens* plant named 'DANDOCHESAL' characterized by having compact, upright and rounded growth habit; salmon colored, double flowers; small, green leaves; and good branching.

2 Drawing Sheets

Latin name of the genus and species of the claimed plant: *Impatiens walleriana.*
Variety denomination: 'DANDOCHESAL'.

BACKGROUND OF THE INVENTION

The present invention relates to a new and distinct cultivar of Double *Impatiens* plant, botanically known as *Impatiens walleriana*, hereinafter referred to by the cultivar name 'DANDOCHESAL'. *Impatiens walleriana*, of the Balsaminaceae family, consists of hardy and tender annual and perennials which are grown in various parts of Asia, North America and South Africa. The new Double *Impatiens* cultivar is a product of a planned breeding program conducted by the inventor, Gabriel Danziger, in Moshav Mishmar Hashiva, Israel. The objective of the breeding program is to develop a new Double *Impatiens* variety with compact, upright and rounded, growth habit; salmon colored flowers; small green leaves and good branching.

The new Double *Impatiens* cultivar originated from a cross made in a controlled breeding program by the inventor in 2000 in Moshav Mishmar Hashiva, Israel. The female parent is designated as '30V' (unpatented). The male parent is designated as '86V' (unpatented). The new Double *Impatiens* cultivar 'DANDOCHESAL' was discovered and selected by the inventor, Gabriel Danziger, as a flowering plant within the progeny of the stated cross in a controlled environment in Moshav Mishmar Hashiva, Israel.

Asexual reproduction of the new cultivar by Stem Tip cutting, was first performed in April, 2001, in Moshav Mishmar Hashiva, Israel, and has demonstrated that the combination of characteristics as herein disclosed for the new cultivar are firmly fixed and retained through successive generations of asexual reproduction. The new cultivar reproduces true-to-type.

BRIEF SUMMARY OF THE INVENTION

The following traits have been repeatedly observed and are determined to be unique characteristics of 'DANDOCHESAL' which in combination distinguish this Double *Impatiens* as a new and distinct cultivar:

1. Compact, upright and rounded growth habit;
2. Salmon colored, double flowers-;

3. Small leaves;
4. Green leaves; and
5. Good branching.

Table 1 provides a comparison among plants of 'DANDOCHESAL' and plants of the parents, '30V' and '86V'.

TABLE 1

| Trait | 'DANDOCHESAL' | Female Parent '30V' (unpatented) | Male Parent '86V' (unpatented) |
|---|---|---|---|
| Flower color | Red group, RHS 38A | Pink: Red purple group, RHS 67C | Pink: Red purple group, RHS 68A |
| Number of Flowers | Approximately 70–80 flowers in full bloom | Approximately 60–70 flowers in full bloom | Approximately 60–70 flowers in full bloom |
| Leaf Color | Green | Green | Green |
| Size of Leaves | Length: 2 cm Width: 2 cm | Length: 4 cm Width: 3 cm | Length: 4 cm, Width: 3 cm |
| Growth and Branching Habit | Very compact growth habit; height 14 cm; strong branching | Medium growth habit; height 25 cm; strong branching | Medium growth habit; height 25 cm; strong branching |
| Flowering time | Full blooming 60 days after planting | Full blooming 60 days after planting | Full blooming 60 days after planting |

Of the many commercial cultivars known to the present inventor, the most similar in comparison to 'DANDOCHESAL' is the Double *Impatiens* cultivar 'DANDOCHESOPINK'. In side-by-side comparisons conducted in Moshav Mishmar Hashiva, Israel, plants of 'DANDOCHESAL' differed from plants of 'DANDOCHESOPINK' primarily in flower color and leaf size, as provided in Table 2.

TABLE 2

| Trait | 'DANDOCHESAL' | 'DANDOCHESOPINK' |
|---|---|---|
| Flower color | Red group, RHS 38A | Red group, RHS 55C |
| Length of leaves | 2 cm | 3 cm |

BRIEF DESCRIPTION OF THE DRAWINGS

The accompanying photographic drawings illustrate the overall appearance of the new Double *Impatiens* cultivar 'DANDOCHESAL' showing the colors as true as is reasonably possible with colored reproductions of this type. Colors in the photographs may differ slightly from the color value cited in the detailed botanical description which accurately describe the color of 'DANDOCHESAL'.

The first photograph shows a side view perspective of a typical flowering potted plant of 'DANDOCHESAL'.

The second photograph shows a close-up view of a single flower of 'DANDOCHESAL'.

DETAILED BOTANICAL DESCRIPTION

The new Double *Impatiens* cultivar 'DANDOCHESAL' has not been observed under all possible environmental conditions. The phenotype of the new cultivar may vary significantly with variations in environment such as temperature, light intensity, and day length without any change in the genotype of the plant.

The aforementioned photographs, together with the following observations, measurements and values describe the new Double *Impatiens* cultivar as grown in a greenhouse in Moshav Mishmar Hashiva, Israel, under conditions which closely approximate those generally used in commercial practice. The new Double *Impatiens* cultivar grew under the typical weather conditions in summer in Israel. Daytime temperatures in summer in Israel are about 30° C. and nighttime temperatures are about 25° C. Fertilization conditions used are N:P:K=5:3:8, N=100 ppm.

Color references are made to The Royal Horticultural Society Color Chart, 2001 ed., except where general colors of ordinary significance are used. Color values were taken under daylight conditions at approximately 12:00 p.m. in Moshav Mishmar Hashiva, Israel. The age of the plant described is 13 weeks from planting.

Classification:
- *Botanical.*—*Impatiens walleriana.*
- *Commercial.*—Double Cheeky Salmon.

Parentage:
- *Female parent.*—'30V' of our breeding program (unpatented).
- *Male parent.*—'86V' of our breeding program (unpatented).

Propagation:
- *Type.*—Stem Tip cutting.
- *Time to initiate roots.*—Approximately 10 days.
- *Time to produce a rooted cutting or liner.*—Approximately 17 days.
- *Time to develop roots.*—Approximately 17 days.
- *Root description.*—Fibrous roots.
- *Rooting habit.*—Adventitious roots from cutting base.

Plant description:
- *Growth and branching habit.*—Compact, upright and rounded growth habit. Strong branching.
- *Crop time.*—8 weeks after planting in a 10–12 cm. pot.
- *General appearance and form.*—Height: 14 cm. Plant spread: Compact, 26 cm.
- *Lateral branches.*—Quantity: Approximately 30 per plant. Length: 8 cm. Diameter: 0.5 cm. Internodes length: 1.0 cm. Texture: Smooth. Branch Color: Yellow-green, RHS 145C.

Foliage:
- *Type.*—Simple.
- *Arrangement.*—Alternate.
- *Overall shape of leaf.*—Ovate.
- *Apex.*—Acuminate.
- *Base.*—Acute.
- *Length.*—2 cm.
- *Width.*—2 cm.
- *Margin.*—Shallowly Serrate.
- *Texture.*—Smooth.
- *Color of upper surface.*—Mature leaf: Green, RHS 143A. Immature leaf: Green, RHS 143B.
- *Color of lower surface.*—Mature leaf: Green, RHS 138B. Immature leaf: Green, RHS 138C.
- *Venation:*
- *Venation pattern.*—Along midrib with secondary veins.
- *Venation color.*—Upper surface: No venation. Lower surface: Green, RHS 138B.
- *Petiole.*—Length: 0.5 cm. Diameter: 3 mm. Texture: Smooth. Color: Green, RHS 138D.

Flowering description:
- *Flowering habit.*—Solitary flowers raised 1 cm above the foliage.
- *Flowering response.*—Flowers at any day length.
- *Flowering season.*—All year round in a greenhouse environment. Flowering is continuous from spring until fall in an outdoor garden.
- *Lastingness of the individual bloom.*—10 days.
- *Quantity of flowers.*—Approximately 5 flowers per stem.
- *Winter hardiness.*—Will resist to 10° C.
- *Fragrance.*—None.
- *Stem.*—Average length: 12 cm. Average diameter: 0.5 cm. Internode length: 1 cm. Texture: Smooth. Color: Yellow-green, RHS 145C.
- *Bud.*—Rate of opening: From the stage that we start to see color until anthesis is 2 days. Shape: Rounded. Length: 0.7 cm. Diameter: 0.5 cm. Color: Red group, RHS 38A.

Inflorescence:
- *Flower type and habit.*—Double flower, day neutral.
- *Overall shape.*—Rosette.
- *Flower size.*—Diameter: 1.5–2 cm. Depth: 0.5 cm.
- *Aspect.*—45°.
- *Borne.*—Above foliage, arising from leaf, upward.
- *Petals.*—Arrangement: Imbricate. Petal Number: 25. Overall Petal Shape: Obcordate. Texture: Smooth. Margin: Entire. Appearance: Uniform color. Petal size for outermost petals: Length: 1.0 cm. Width: 1.0 cm. Petal size for innermost petals: Length: 0.5 cm. Width: 0.1 cm. Petal Color (when first opening): Upper surface: Orange red group, RHS 33D. Lower surface: Red group, RHS 38C. Petal Color (when fully opened): Upper surface: Orange red group, RHS 33D. Lower surface: Red group, RHS 38B. Petal color fading to: Red group, RHS 49B.
- *Calyx.*—Quantity of sepals: 3 sepals with lower sepal modified into a spur. Sepal texture: Smooth. Sepal shape: Apex shape of sepals: Acuminate. Overall shape of lateral sepals: Oblanceolate. Overall shape of lower sepal (sepal modifies into spur): Elliptic. Sepal size: Lateral sepal length: 2 mm. Lateral sepal width: 1 mm. Lower sepal length: 8 mm. Lower sepal width: 5 mm. Sepal Color: Lateral sepal color: Yellow-green group, RHS 144D. No difference in color between apex and base. Lower sepal color: Base: Violet group, RHS 84D. Apex: White group, RHS 155A.
- *Spur.*—Quantity per flower: 1. Length: 1.7 cm. Diameter at base: 2.0 mm. Diameter at tip: 0.5 mm. Color: Base: White group, RHS 155C. Tip: Greyed-purple group, RHS 186C.

*Peduncles.*—Length: 1.5 cm. Diameter: 1.0 mm. Texture: Smooth. Strength: Strong but flexible. Angle to stem: Acute.

Reproductive organs: Sterile, no reproductive organs.

Disease resistance: No sensibility was observed under regular growing conditions.

I claim:

1. A new and distinct Double *Impatiens* plant named 'DANDOCHESAL', substantially as illustrated and described herein.

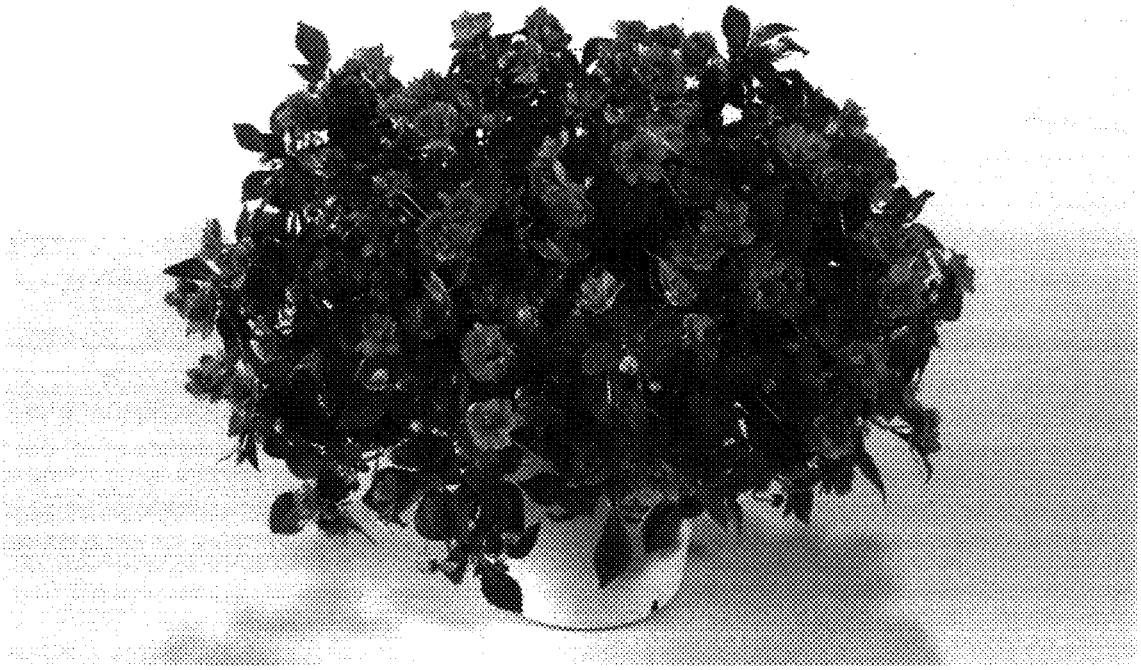

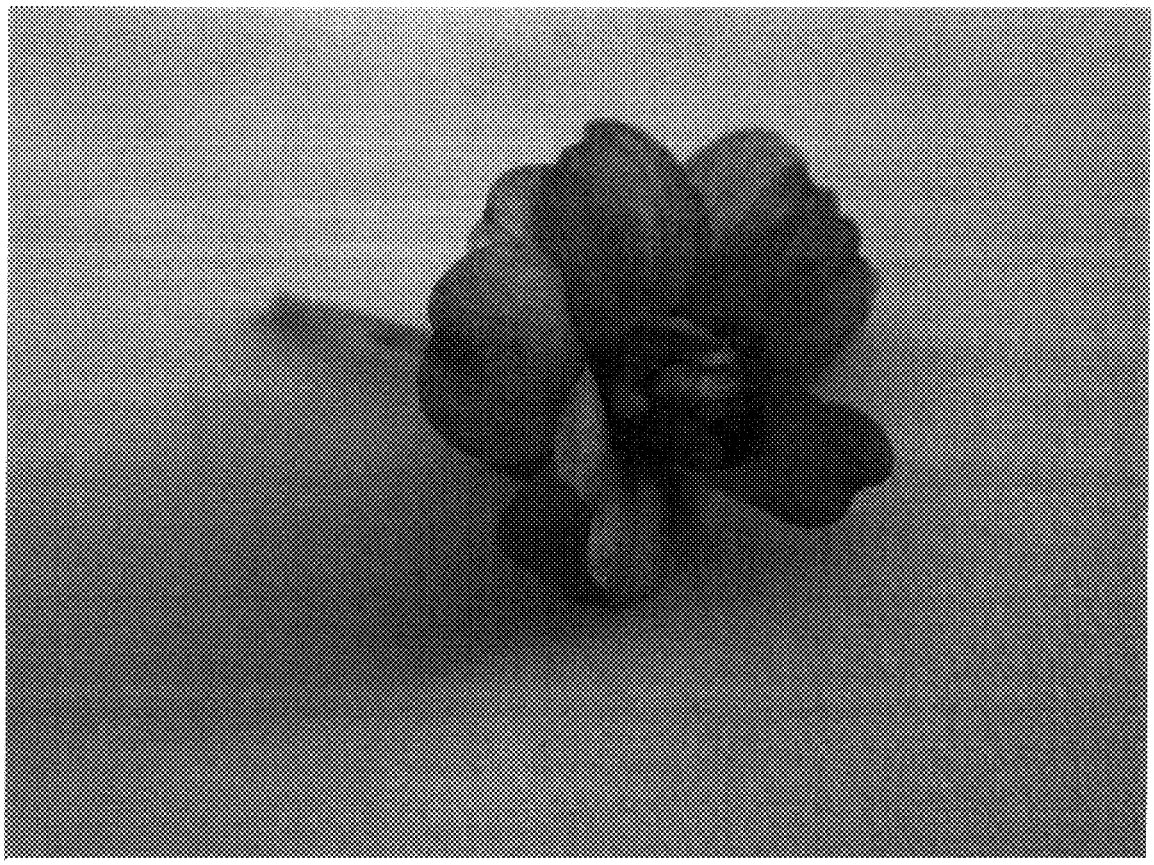

* * * * *